United States Patent

Ando et al.

[11] Patent Number: 5,078,989
[45] Date of Patent: Jan. 7, 1992

[54] SKIN WHITENING COSMETICS

[75] Inventors: Hideya Ando; Mitsuaki Shimizu, both of Kyoto; Akira Hashimoto; Hisatoya Kato, both of Osaka; Yoshitsugu Ozasa, Shiga, all of Japan

[73] Assignee: Sunstar K.K., Osaka, Japan

[21] Appl. No.: 501,816

[22] Filed: Mar. 28, 1990

[51] Int. Cl.$^5$ .............. A61K 7/021; A01N 43/08
[52] U.S. Cl. ..................... 424/62; 424/489; 514/474; 514/844; 514/846; 514/937
[58] Field of Search .......... 424/62, 489, 69; 514/474, 844, 846, 937

[56] References Cited

U.S. PATENT DOCUMENTS

| | | | |
|---|---|---|---|
| 4,572,915 | 2/1986 | Crooks | 514/458 |
| 4,792,443 | 12/1988 | Filomeno | 424/62 |
| 4,818,521 | 4/1989 | Tomabuchi | 424/62 |

FOREIGN PATENT DOCUMENTS

| | | | |
|---|---|---|---|
| 55020739 | 7/1978 | Japan | 424/62 |
| 56-120612 | 2/1980 | Japan | 424/62 |
| 61030510-A | 7/1984 | Japan | 424/62 |
| 339632 | 8/1959 | Switzerland . | |

Primary Examiner—Thurman K. Page
Attorney, Agent, or Firm—Sughrue, Mion, Zinn, Macpeak & Seas

[57] ABSTRACT

A cosmetic comprising a compound represented by formula (I) is disclosed:

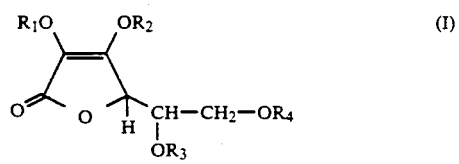

wherein $R_1$, $R_2$, $R_3$ and $R_4$, which may be the same or different, each represents a hydrogen atom or $CH_3(CH_2)_3(CH_2CH=CH)_2(CH_2)_7CO-$, provided that at least one of $R_1$, $R_2$, $R_3$ and $R_4$ is not a hydrogen atom.

8 Claims, No Drawings

SKIN WHITENING COSMETICS

FIELD OF THE INVENTION

The present invention relates to a skin whitening cosmetic for eliminating, reducing or preventing skin browning due to ultraviolet light or pigmentation in the skin, e.g., spots or freckles, and more particularly to a cosmetic comprising a base for cosmetics and a linoleic acid-vitamin C ester.

BACKGROUND OF THE INVENTION

Known cosmetics for giving fairness to the facial skin include compositions containing vitamin C or derivatives thereof, reducing agents, or a tyrosinase inhibitor, e.g., a placenta extract. These conventional skin whitening cosmetics exhibit inhibitory activity against melanin production when tested in vitro using tissue cultures. However, they have not succeeded in obtaining sufficient effects on elimination or reduction of pigmentation when actually applied to the skin.

SUMMARY OF THE INVENTION

An object of the present invention is to provide a cosmetic which exhibits excellent skin whitening effects without any adverse side effects when actually applied to the skin.

Other objects and effects of the present invention will be apparent from the following description.

The inventors have conducted extensive investigations and, as a result, found that a linoleic acid-vitamin C ester produces excellent effects on elimination and reduction of pigments deposited in the skin and thus attained the present invention.

That is, the present invention relates to a skin whitening cosmetic containing a compound represented by formula (I):

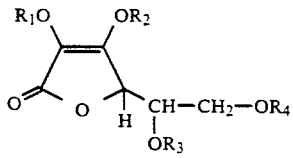

wherein $R_1$, $R_2$, $R_3$ and $R_4$, which may be the same or different, each represents a hydrogen atom or $CH_3(CH_2)_3(CH_2CH=CH)_2(CH_2)_7CO-$, provided that at least one of $R_1$, $R_2$, $R_3$ and $R_4$ is not a hydrogen atom.

DETAILED DESCRIPTION OF THE INVENTION

Linoleic acid-vitamin C esters which can be used in the present invention typically include ascorbyl 6-monolinoleate, ascorbyl 5-monolinoleate, ascorbyl 2,5-dilinoleate, ascorbyl 2,6-dilinoleate, ascorbyl 2,5,6-trilinoleate and ascorbyl 3,5,6-trilinoleate. These compounds may be used either individually or in combinations of two or more thereof.

Among these compounds, ascorbyl 6-monolinoleate, ascorbyl 2,6-dilinoleate and ascorbyl 2,5,6-trilinoleate, and more preferably ascorbyl 6-monolinoleate and ascorbyl 2,6-dilinoleate, are preferably used in the present invention.

Linoleic acid-vitamin C esters have been known to have the same activities as vitamin C or anti-inflammatory activity as described in Swiss Patent 339,632 but have not yet been known to have a skin whitening effect.

The linoleic acid-vitamin C esters can be prepared by conventional processes for ester synthesis (as described, e.g., in Swiss Patent 339,632 incorporated herein by reference), for example, by the reaction between linoleic acid chloride and ascorbic acid (vitamin C). These processes produce a mixture of linoleic acid-vitamin C esters. In the present invention, such a mixed ester may be used either as it is or after being separated into each ester.

A proportion of the linoleic acid-vitamin C ester(s) in the cosmetic of the present invention is not particularly limited and may be selected from a broad range. It is generally from 0.01 to 10% by weight, preferably from 0.05 to 5% by weight, more preferably from 0.5 to 5% by weight, and particularly preferably from 1 to 5% by weight, based on the total amount of the cosmetic of the present invention.

The skin whitening effect of the linoleic acid-vitamin C esters of the present invention was tested as follows in comparison with other various conventional compounds.

Test Method

Ultraviolet light (UVB intensity: 1 J/cm$^2$) was irradiated on the shaved back of English brown guinea pigs. One week later, a pigmentation was formed.

A linoleic acid-vitamin C ester, vitamin C or other test compound were dissolved in a 70% aqueous solution of ethanol to prepare solutions. The solutions each was then repeatedly applied over 4 weeks on the back of the guinea pigs having the pigmentation. The coated amount was 0.1 ml/cm$^2$ once per day.

The degree of pigmentation was evaluated based on the following rating system.
0: No reduction of pigmentation was observed (corresponding to the degree of pigmentation on the skin area where no test compound was applied.)
−1: Slight reduction in pigmentation was observed.
−2: Reduction in pigmentation was observed.

The results of the evaluation are shown in Table 1 below.

TABLE 1

| Test Compound | Concentration (w/v %) | Degree of Pigmentation |
| --- | --- | --- |
| None | — | 0 |
| Vitamin C | 1 | 0 |
| Vitamin C | 5 | 0 |
| Ascorbyl 6-palmitate | 1 | 0 |
| Ascorbyl 6-palmitate | 5 | 0 |
| Ascorbyl 6-stearate | 1 | 0 |
| Ascorbyl 6-stearate | 5 | 0 |
| Ascorbyl 6-linoleate | 1 | −1 |
| Ascorbyl 6-linoleate | 5 | −2 |
| Ascorbyl 2,6-dilinoleate | 1 | −1 |
| Ascorbyl 2,6-dilinoleate | 5 | −2 |
| Ascorbyl 2,5,6-trilinoleate | 1 | −2 |
| Ascorbyl 2,5,6-trilinoleate | 5 | −2 |
| Placenta extract | 1 | 0 |
| Placenta extract | 5 | 0 |

As is apparent from the results in Table 1, linoleic acid-vitamin C esters, such as ascorbyl 6-monolinoleate, ascorbyl 2,6-dilinoleate and ascorbyl 2,5,6-trilinoleate exhibit, significant effects on reduction of pigmentation, whereas no such effects are observed in vitamin C or esters thereof with other straight chain saturated fatty acid esters. The cosmetics of the present invention can be formulated into lotions, cosmetic oils, creams, emulsions (or milky lotions), masks (or packs), powders, and so on according to known techniques. For example, the linoleic acid-vitamin C esters may be directly incorporated into cosmetic compositions, such as creams and milky lotions, or may be previously dissolved in an oil phase component of these cosmetic compositions. Also, they may be dissolved in an appropriate solvent, such as alcohols, and then formulated into cosmetics by emulsification, mixing, dispersion, or dissolution.

The cosmetic compositions which can be used in the present invention are not particularly limited and may be any conventional compositions as long as the effects of the present invention are not impaired.

If desired, the cosmetics of the present invention may further contain other conventional components as long as the effects of the present invention are not impaired.

The conventional compositions and its production process as well as the conventional components added therefor of the cosmetic compositions are described, e.g., in *Keshohin-Gaku* (Cosmetic Science), edited by T. Ikeda, published on May 20, 1979 by Nanzando, Japan, which is incorporated herein by reference, but the present invention is not construed as being limited thereto. Related portions of this reference are shown in Table 2 below.

TABLE 2

| Cosmetics | Compositions and production process | Other components |
| --- | --- | --- |
| Lotions | page 220, line 14 to page 221, line 12 up | page 251, Table 31 |
| Creams | page 235, line 9 up to page 236, line 6 up | page 227, line 6 up to page 228, line 5 |
| Emulsions | page 243, line 10 to page 244 | page 242, line 12 to line 6 up |
| Packs | page 246, line 11 to page 248 | page 245, line 16 to line 21 |
| Powders | page 253, line 3 to page 255, line 8 up | page 251, line 10 to page 253, line 2 |

Furthermore, if desired, the cosmetics of the present invention can contain various conventional additives, such as melanin production inhibitors (whitening agents) (e.g., straight chain saturated fatty acid esters of vitamin C and placenta extract), ultraviolet absorbents, ultraviolet scattering agents, anti-inflammatory agents, and antioxidants, as long as the effects of the present invention are not impaired.

Examples of the conventional additives and their addition amounts are shown in Table 3 below but they are not limited thereto. The addition amounts are shown in terms of percent by weight (except Vitamin A) based on the total amount of the cosmetic compositions.

TABLE 3

| Additives | Addition amount (% by weight) |
| --- | --- |
| Whitening agent | |
| Placenta extract | 0.1 to 3 |
| Kojic acid | 0.1 to 3 |
| Photosensitive element No. 201 | 0.0001 to 0.002 |
| Plant extract | 0.01 to 1 |
| Vitamin A | 500 IU to 2,500 IU |
| Anti-inflammatory agent | |
| Dipotassium grycyrrhizic acid | 0.01 to 0.2 |
| Stearil grycyrrethinate | 0.01 to 0.2 |
| Allantoin | 0.01 to 0.2 |

TABLE 3-continued

| Additives | Addition amount (% by weight) |
| --- | --- |
| ε-Aminocaproic acid | 0.01 to 0.1 |
| Methyl salicylate | 0.01 to 0.1 |
| Ultraviolet absorbent | |
| Urocanic acid | 0.01 to 1 |
| 2-Ethoxyethyl 4-methoxycinnamate | 0.01 to 5 |
| Ethyl paraaminobenzoate | 0.01 to 4 |
| Oxybenzone | 0.01 to 5 |
| Octyl salicylate | 0.01 to 0.1 |
| Ultraviolet scattering agent | |
| Titanium oxide | 0.1 to 10 |
| Zinc oxide | 0.1 to 10 |
| Kaolin | 0.1 to 20 |
| Talc | 0.1 to 30 |
| Magnesium silicate | 0.1 to 10 |
| Antioxidant | |
| Dibutylhydroxytoluene | 0.01 to 1 |
| Butylhydroxyanisole | 0.01 to 1 |
| Propyl gallate | 0.01 to 0.2 |
| Tocopherol | 0.01 to 1 |
| Erythorbic acid | 0.0001 to 0.05 |

The cosmetics according to the present invention can be applied to the skin by conventional manners. For example, a lotion containing 1 wt % of the compound of the present invention can be applied by hands 1 to several times per day; one or two drops of a cosmetic oil containing 3 wt % of the compounds can be applied to the portion at which pigmentation occurs by fingers 1 to 3 times per day; a cream containing 5 wt % of the compound can be applied by hands 1 to several times per day; an emulsion containing 2 wt % of the compound can be applied by hands 1 to 3 times per day; and a pack can be used in such a manner that 5 to 10 g of the pack is applied to the facial skin other than eyes and nose, and it allows to stand for about 30 minutes followed by being removed 1 to 2 times per week.

The present invention is now illustrated in greater detail by way of the following Examples, but it should be understood that the present invention is not deemed to be limited thereto. All the percents are by weight unless otherwise indicated.

EXAMPLE 1

| Lotion: | |
| --- | --- |
| Ascorbyl 6-monolinoleate | 1.0% |
| Glycerin | 6.0% |
| Ethanol | 8.0% |
| Polyoxyethylene hydrogenated castor oil (60 E.O.) | 0.8% |
| Methyl p-hydroxybenzoate | 0.05% |
| Citric acid | 0.05% |
| Sodium citrate | 0.07% |
| Flavor | 0.1% |
| Water-soluble placenta extract | 2.0% |
| Purified water | balance |

Glycerin, citric acid, sodium citrate and water-soluble placenta extract were dissolved in purified water. Separately, ascorbyl 6-monolinoleate, polyoxyethylene hydrogenated castor oil (60E.O.), methylparaben (i.e., methyl p-hydroxybenzoate) and the flavor were dissolved in ethanol, and the ethanol solution was added to the above prepared aqueous solution. The mixture was filtered to obtain a lotion. The flavors used in the examples were conventional flavors generally used for cosmetics.

EXAMPLE 2

| Cosmetic Oil: | |
| --- | --- |
| Ascorbyl 2,6-dilinoleate | 3.0% |
| Ethyl linoleate | 1.0% |
| Retinol acetate | 0.3% |
| Cholesteryl stearate | 1.0% |
| Olive oil | 2.0% |
| Squalane | balance |

In squalane were uniformly dissolved other components to obtain a beauty oil.

EXAMPLE 3

| Cream: | |
| --- | --- |
| Component A: | |
| Ascorbyl 6-monolinoleate | 5.0% |
| d,l-α-Tocopheryl acetate | 0.2% |
| Bleached bees wax (White Wax) | 4.0% |
| Cetanol | 2.0% |
| Linoleic acid | 1.0% |
| Lanolin | 2.0% |
| Liquid paraffin | 9.0% |
| Self-emulsifiable glycerol monostearate | 3.0% |
| Polyoxyethylene sorbitan monostearate (20 E.O.) | 1.5% |
| Propyl p-hydroxybenzoate | 0.1% |
| Component B: | |
| Methyl p-hydroxybenzoate | 0.2% |
| Propylene glycol | 5.0% |
| Flavor | 0.2% |
| Purified water | balance |

A mixture of components A was heat-melted and kept at 80° C. Separately, a mixture of components B other than the flavor was heat-melted and kept at 80° C., and the molten mixture of components A was added thereto while stirring. After sufficient mixing was stirring, the mixture was cooled while stirring, and the flavor was added thereto, followed by cooling to obtain a cream.

EXAMPLE 4

| Emulsion: | |
| --- | --- |
| Component A: | |
| Ascorbyl 2,6-dilinoleate | 2.0% |
| Stearyl glycyrrhetinate | 0.1% |
| Liquid paraffin | 5.0% |
| Vaseline | 2.0% |
| Bees wax | 1.0% |
| Sorbitan sesquioleate | 2.0% |
| Component B: | |
| Polyoxyethylene oleyl ether (20 E.O.) | 2.5% |
| Ethyl p-hydroxybenzoate | 0.2% |
| Propylene glycol | 5.0% |
| Carboxyvinyl polymer | 0.5% |
| Potassium hydroxide | 0.3% |
| Flavor | 0.2% |
| Purified water | balance |

A mixture of components A was heat-melted and kept at 80° C. Separately, a mixture of components B other than the flavor was heat-melted and kept at 80° C., and the molten mixture of components A was added thereto while stirring. After sufficient mixing with stirring, the mixture was cooled while stirring, and the flavor was added thereto, followed by cooling to obtain an emulsion.

EXAMPLE 5

| Pack: | |
| --- | --- |
| Ascorbyl 2,5,6-trilinoleate | 5.0% |
| Oil-soluble placenta extract | 2.0% |
| Vinyl acetate-styrene copolymer | 10.0% |
| Polyvinyl alcohol | 10.0% |
| Sorbitol | 5.0% |
| Titanium oxide | 8.0% |
| Kaolin | 7.0% |
| Ethanol | 5.0% |
| Flavor | 2.0% |
| Ethyl p-hydroxybenzoate | 0.2% |
| Purified water | balance |

Ascorbyl 2,5,6-trilinoleate, the flavor, and ethanol were uniformly mixed to form a solution, and the solution was added to a uniform mixture of the vinyl acetate-styrene copolymer, polyvinyl alcohol, sorbitol, titanium oxide, and kaolin. To the mixture was further added a uniform solution of the oil-soluble placenta extract and ethyl p-hydroxybenzoate in purified water, followed by uniformly mixing to obtain a pack.

The cosmetics according to the present invention, when applied to the skin, exhibit excellent effects to eliminate or reduce browning due to a suntan or pigmentation in the skin.

While the invention has been described in detail with reference to specific embodiments thereof, it will be apparent to one skilled in the art that various changes and modifications can be made therein without departing from the spirit and scope thereof.

We claim:

1. A cosmetic in the form selected from the group consisting of lotion, oils, cream, emulsion, pack and powders comprising a compound represented by formula (I)

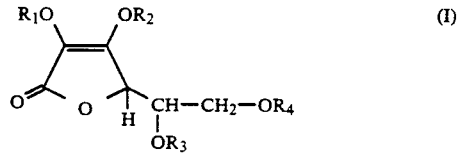

wherein $R_1$, $R_2$, $R_3$ and $R_4$, which may be the same or different, each represents a hydrogen or $CH_3(CH_2)_3(CH_2CH=CH)_2(CH_2)_7CO-$, provided that at least one of $R_1$, $R_2$, $R_3$ and $R_4$ is not a hydrogen atom, wherein said compound represented by formula (I) is present in an amount from 0.01 to 10% by weight based on the total amount of said cosmetic.

2. A cosmetic as claimed in claim 1, wherein said compound represented by formula (I) is selected from the group consisting of ascorbyl 6-monolinoleate, ascorbyl 5-monolinoleate, ascorbyl 2,5-dilinoleate, ascorbyl 2,6-dilinoleate, ascorbyl 2,5,6-trilinoleate, ascorbyl 3,5,6-trilinoleate and mixtures thereof.

3. A cosmetic as claimed in claim 2, wherein said compound represented by formula (I) is selected from the group consisting of ascorbyl 6-monolinoleate, ascorbyl 2,6-dilinoleate and ascorbyl 2,5,6-trilinoleate.

4. A cosmetic as claimed in claim 3, wherein said compound represented by formula (I) is selected from the group consisting of ascorbyl 6-monolinoleate and ascorbyl 2,6-dilinoleate.

5. A cosmetic as claimed in claim 1, wherein said compound represented by formula (I) is present in an amount from 0.05 to 5% by weight based on the total amount of said cosmetic.

6. A cosmetic as claimed in claim 9, wherein said compound represented by formula (I) is present in an amount from 0.05 to 5% by weight based on the total amount of said cosmetic.

7. A cosmetic as claimed in claim 6, wherein said compound represented by formula (I) is present in an amount from 1 to 5% by weight based on the total amount of said cosmetic.

8. A cosmetic as claimed in claim 1 in the form of a milky lotion.

* * * * *

UNITED STATES PATENT AND TRADEMARK OFFICE
CERTIFICATE OF CORRECTION

PATENT NO. : 5,078,989

DATED : January 7, 1992

INVENTOR(S) : Hideya ANDO et al

It is certified that error appears in the above-identified patent and that said Letters Patent is hereby corrected as shown below:

In claim 6, at line 1, (at line 3 of column 7), delete "9" and insert therefor --1--;

at line 3, (at line 5 of column 7), delete "0.05" and insert therefor --0.5--.

Signed and Sealed this

Thirteenth Day of April, 1993

Attest:

STEPHEN G. KUNIN

*Attesting Officer*     *Acting Commissioner of Patents and Trademarks*